United States Patent
Sawchuk et al.

(10) Patent No.: US 7,123,963 B2
(45) Date of Patent: Oct. 17, 2006

(54) METHOD OF AUTOMATIC EVOKED RESPONSE SENSING VECTOR SELECTION USING EVOKED RESPONSE WAVEFORM ANALYSIS

(75) Inventors: Robert T. Sawchuk, Lino Lakes, MN (US); Michael W. Heinks, New Brighton, MN (US); David W. Graden, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 547 days.

(21) Appl. No.: 10/284,870

(22) Filed: Oct. 31, 2002

(65) Prior Publication Data

US 2004/0088018 A1    May 6, 2004

(51) Int. Cl.
*A61N 1/18* (2006.01)
(52) U.S. Cl. .......................... 607/27; 607/28
(58) Field of Classification Search ............. 607/4–5, 607/14, 27–28, 123, 148
See application file for complete search history.

(56) References Cited

U.S. PATENT DOCUMENTS

| | | | |
|---|---|---|---|
| 4,502,492 A | 3/1985 | Bornzin | 128/785 |
| 4,549,548 A | 10/1985 | Wittkampf et al. | 128/419 PG |
| 4,628,934 A | 12/1986 | Pohndorf et al. | 128/419 |
| 5,117,824 A | 6/1992 | Keimel et al. | 128/419 D |
| 5,222,493 A | 6/1993 | Sholder | 128/419 |
| 5,324,310 A | 6/1994 | Greeninger et al. | 607/28 |
| 5,331,966 A | 7/1994 | Bennett et al. | 128/696 |
| 5,417,718 A | 5/1995 | Kleks et al. | |
| 5,683,431 A | 11/1997 | Wang | 607/28 |
| 5,707,398 A | 1/1998 | Lu | 607/27 |
| 5,855,594 A | 1/1999 | Olive et al. | 607/28 |
| 5,861,013 A * | 1/1999 | Peck et al. | 607/28 |
| 6,085,118 A | 7/2000 | Hirschberg et al. | 607/9 |
| 6,134,473 A | 10/2000 | Hemming et al. | 607/28 |
| 6,430,448 B1 | 8/2002 | Chitre et al. | 607/121 |
| 6,434,428 B1 | 8/2002 | Sloman et al. | 607/28 |
| 6,643,546 B1 * | 11/2003 | Mathis et al. | 607/9 |
| 6,782,291 B1 * | 8/2004 | Bornzin et al. | 607/28 |
| 2001/0049543 A1 | 12/2001 | Kroll | 607/28 |
| 2002/0116031 A1 | 8/2002 | Vonk | 607/28 |
| 2003/0050371 A1 * | 3/2003 | Bradley | 607/27 |
| 2003/0083709 A1 * | 5/2003 | Zhu et al. | 607/27 |
| 2003/0083710 A1 * | 5/2003 | Ternes et al. | 607/27 |
| 2003/0195579 A1 * | 10/2003 | Bradley et al. | 607/27 |

FOREIGN PATENT DOCUMENTS

| EP | 1184050 A2 | 3/2002 |
|---|---|---|
| WO | WO 01/43820 A1 | 6/2001 |
| WO | WO 03/092807 A1 | 11/2003 |

\* cited by examiner

*Primary Examiner*—Robert E. Pezzuto
*Assistant Examiner*—Tammie K. Heller
(74) *Attorney, Agent, or Firm*—Michael C. Soldner; Girma Wolde-Michael

(57) ABSTRACT

A cardiac pacing device and method for automatically selecting an optimal evoked response sensing vector based on an evaluation of the evoked response signal quality are provided. Electrode switching circuitry allows selection of multiple sensing electrode vectors. Capture detection circuitry provides capture and loss of capture signal characteristics determined during a pacing threshold search to be used in determining evoked response signal quality parameters. An optimal evoked response sensing vector is selected based on evoked response signal quality parameters meeting predetermined criteria for reliable evoked response sensing.

23 Claims, 11 Drawing Sheets

METHOD OF AUTOMATIC EVOKED RESPONSE SENSING VECTOR SELECTION USING EVOKED RESPONSE WAVEFORM ANALYSIS

FIELD OF THE INVENTION

The present invention relates to implantable cardiac pacemaking devices and, more specifically, to an implantable pacemaking device and method for automatically selecting an optimal electrode vector for sensing evoked responses to verify capture.

BACKGROUND OF THE INVENTION

Cardiac pacing devices deliver appropriately timed electrical stimulation pulses to a patient's heart to maintain a normal heart rhythm or improve synchronization of heart chambers. Patients having bradycardia, abnormalities of the heart's natural conduction system, or heart failure may benefit from artificial cardiac pacing of one or more heart chambers. In order to effectively pace the heart, an electrical impulse delivered to the heart must have sufficient energy to depolarize the myocardial cells. Depolarization of the myocardial cells in response to a pacing pulse is often referred to as "capture." The cardiac electrogram signal evidencing capture, which may be a P-wave in the atria or an R-wave in the ventricles, is generally referred to as an "evoked response." The lowest pacing pulse energy that captures the heart may be referred to as the "pacing threshold" or "capture threshold". The amplitude and duration of a pacing pulse are preferably set to provide a pacing pulse energy somewhat greater than the pacing threshold in order to ensure effective cardiac pacing. However, in order to prolong the battery life of the implanted pacemaking device, it is desirable to program the pacing pulse energy to be a minimum value that is considered safely above the pacing threshold.

Pacing threshold however can change over time due to fibrotic encapsulation of the pacing electrodes, changes in the patient's clinical condition, changes in medical therapy, lead movement, or other causes. A rise in pacing threshold can result in loss of capture and ineffective pacing. Modern pacemakers, therefore, may include automatic pacing threshold search algorithms that automatically adjust the pacing pulse energy to ensure pacing pulses remain above the pacing threshold, even if it varies over time. A pacing threshold search may deliver pacing pulses starting at an initially high pulse energy that is greater than the pacing threshold and progressively decrease until capture is lost. The lowest pulse energy at which capture still occurs is determined as the pacing threshold. In order to reliably determine a pacing threshold, the cardiac pacing device must reliably discriminate between capture and loss of capture.

One method that has been implemented in commercially available devices for detecting capture is to sense the evoked response following a pacing pulse. Evoked response sensing may be to verify capture during pacing threshold searches and during normal cardiac pacing to ensure that effective pacing is provided. If a loss of capture is detected, as evidenced by the absence of an evoked response following a pacing pulse, a back-up pacing pulse of higher energy may be delivered and a pacing threshold search may be triggered to reset the pacing pulse energy.

Accurate capture verification and maintenance of effective cardiac pacing therefore depends on reliable evoked response sensing. False capture detection can result from oversensing of cardiac signals or non-cardiac noise, such as electromagnetic interference or nearby skeletal muscle depolarizations. False capture detections may result in prolonged episodes of subthreshold cardiac pacing that is ineffective in maintaining a base heart rate, which can be detrimental to the patient's health and even fatal. False loss of capture detections can result from undersensing of the evoked response. False loss of capture detections can trigger the delivery of unnecessary backup pacing pulses and pacing threshold searches. Increases in pacing pulse energy due to false loss of capture detections can lead to premature pacemaker battery depletion.

A major difficulty in sensing an evoked response arises from the polarization artifact that immediately follows a pacing pulse. Polarization at the electrode-tissue interface causes an afterpotential signal that can saturate sense amplifiers included in the cardiac pacing device and mask an evoked response signal. Typically, a blanking interval is applied to sense amplifiers during and immediately following a pacing pulse to prevent saturation of the amplifiers. The polarization artifact may diminish during the blanking interval, however, it may still interfere with evoked response sensing. Low-polarization electrodes have been proposed for reducing the polarization artifact. See for example U.S. Pat. No. 4,502,492, issued to Bornzin, or U.S. Pat. No. 6,430,448, issued to Chitre, et al.

Improved methods for performing capture verification based on evoked response sensing have been proposed. Such methods may include special hardware circuitry or special software signal processing methods that reduce or eliminate the problem of polarization artifact. Reference is made to commonly assigned U.S. Pat. No. 6,134,473, issued to Hemming et al. and U.S. Pat. Application No. 20020116031 issued to Vonk, incorporated herein by reference in their entirety. Capture verification methods indicate when capture or loss of capture occurs, but generally do not indicate the confidence or reliability of the detection based on the quality of the evoked response signal. A process to verify capture that involves assessing the reliability of a chosen parameter of an evoked signal as a reliable indication of the response is disclosed in U.S. Pat. No. 5,855,594, issued to Olive, et al, incorporated herein by reference. The reliability of a sensed parameter will depend largely on the quality of the sensed signal. A sensed parameter that is not reliable for evoked response sensing on one sensing electrode pair may be reliable using another sensing electrode pair.

Cardiac pacing leads are often configured having a tip electrode and a ring electrode spaced somewhat back from the tip electrode. Bipolar pacing between the tip and ring electrode is often preferred over unipolar pacing between the tip electrode and pacing device housing because bipolar pacing thresholds can be lower than unipolar. Bipolar sensing of intrinsic cardiac P-waves and/or R-waves for monitoring a patient's intrinsic heart rate to determine the need for pacing can also be preferred over unipolar sensing because bipolar sensing can result in a better signal-to-noise ratio. Bipolar sensing of intrinsic signals can be improved further by shortening the spacing between a tip electrode and a ring electrode to reduce oversensing of far-field cardiac signals or non-cardiac noise. However, a shorter tip-to-ring spacing can make bipolar evoked response sensing more difficult because the evoked response signal may have already passed the ring electrode by the time the polarization signal has diminished.

Selection of separate sensing electrodes for sensing the evoked response, different than the electrode pair used for delivering the pacing pulse, can reduce or eliminate polarization artifact problems. Sensing a far-field signal related to an evoked response, as opposed to the near-field evoked response signal, or sensing a conducted polarization away from the pacing site has been proposed. See for example, U.S. Pat. No. 5,324,310 issued to Greeninger, U.S. Pat. No. 5,222,493 issued to Sholder, U.S. Pat. No. 5,331,966 issued to Bennett et al., U.S. Pat. No. 6,434,428 issued to Sloman, et al., and U.S. Pat. App. No. 20010049543, issued to Kroll. In pacing systems having alternative sensing electrodes available and programmable selection of sensing electrodes, alternate sensing electrodes may be selected if capture detection is inadequate using a default evoked response sensing electrode pair. However, manual selection of an optimal evoked response sensing electrode pair can be a time-consuming process and can be "hit-or-miss" since only capture or loss of capture information is generally provided without information regarding the evoked response signal quality.

Automatic switching of electrode polarity in cardiac pacing devices has also been proposed. Electrode switching/selection is generally disclosed in U.S. Pat. No. 4,628,934 issued to Pohndorf et al., and U.S. Pat. No. 6,085,118 issued to Hirschberg et al., both of which are incorporated herein by reference. Automatic switching between unipolar and bipolar operation during each pacer cycle to optimize the choice of unipolar and bipolar operation for given pacemaker events is generally disclosed in U.S. Pat. No. 4,549,548 issued to Wittkampf, et al., incorporated herein by reference. In the '428 patent cited above, switching between bipolar sensing in the atrium and unipolar sensing during a far-field interval window for detecting far-field R-waves for verification of atrial capture is generally disclosed.

However, automatic switching/selection of electrodes does not necessarily ensure that an optimal evoked response sensing electrode configuration will be selected. When multiple electrodes are available, evoked response sensing may be more reliable along one sensing vector than another. A method for automatically determining an optimal electrode configuration for measuring a metabolic parameter such as minute volume used for metabolic rate responsive pacemakers is generally disclosed in U.S. Pat. No. 5,707,398, issued to Lu. This method, however, does not address optimal electrode determination of evoked response sensing. What is needed therefore, is a method for automatically selecting an optimal evoked response sensing vector based on an evaluation of the evoked response signal quality.

SUMMARY OF THE INVENTION

The present invention provides an implantable cardiac pacing device and method for automatically selecting an optimal evoked response sensing vector based on an evaluation of the evoked response signal quality. The pacing device preferably includes electrode switching circuitry to enable selection of multiple evoked response sensing vectors. The pacing device further includes capture detection circuitry that provides output relating to one or more signal characteristics that may be used for determining one or more evoked response signal quality parameters. In a preferred embodiment, the capture detection circuitry includes a peak tracking circuit for detecting one or more peak amplitudes of capture and loss of capture signals during a capture detection window. The times at which peak amplitudes occur may also be determined. The peak amplitude information is used to determine signal quality parameters, which preferably include at least an evoked response signal-to-noise ratio and an evoked response sensing margin. Other signal quality evaluation parameters may be related to a loss of capture sensing margin, early or latent capture detections, and time to evoked response peak amplitude.

A method for optimizing the evoked response sensing vector is executed when a pacing threshold search is performed in order to validate the result of the pacing threshold search and select an optimal sensing vector for use in capture detection. An optimal evoked response sensing vector is determined as a sensing vector for which evoked response signal quality parameters meet predetermined criteria for reliable evoked response sensing. Signal characteristics are determined from capture signals and from loss of capture signals during the pacing threshold search using a default evoked response sensing vector. Signal quality parameters are then determined from the signal characteristics. If the signal quality parameters meet predetermined criteria, the pacing threshold search result is deemed valid and the default sensing vector and sensing threshold may be programmed as the operating evoked response sensing vector and threshold. If the signal quality is unacceptable, the pacing threshold search result is deemed invalid, and alternative sensing vectors are tested until an acceptable vector is identified. Alternatively, all available sensing vectors may be tested and the vector producing the best signal quality may be selected as the operating evoked response sensing vector during capture verification.

The device and method of the present invention, therefore, allow the quality of evoked response signals to be evaluated automatically so that evoked response sensing may be optimized. Optimized evoked response sensing will allow automatic capture verification operations and pacing threshold search algorithms to perform more reliably, improving overall cardiac pacing device performance and longevity.

DETAILED DESCRIPTION OF THE INVENTION

Figure 1:
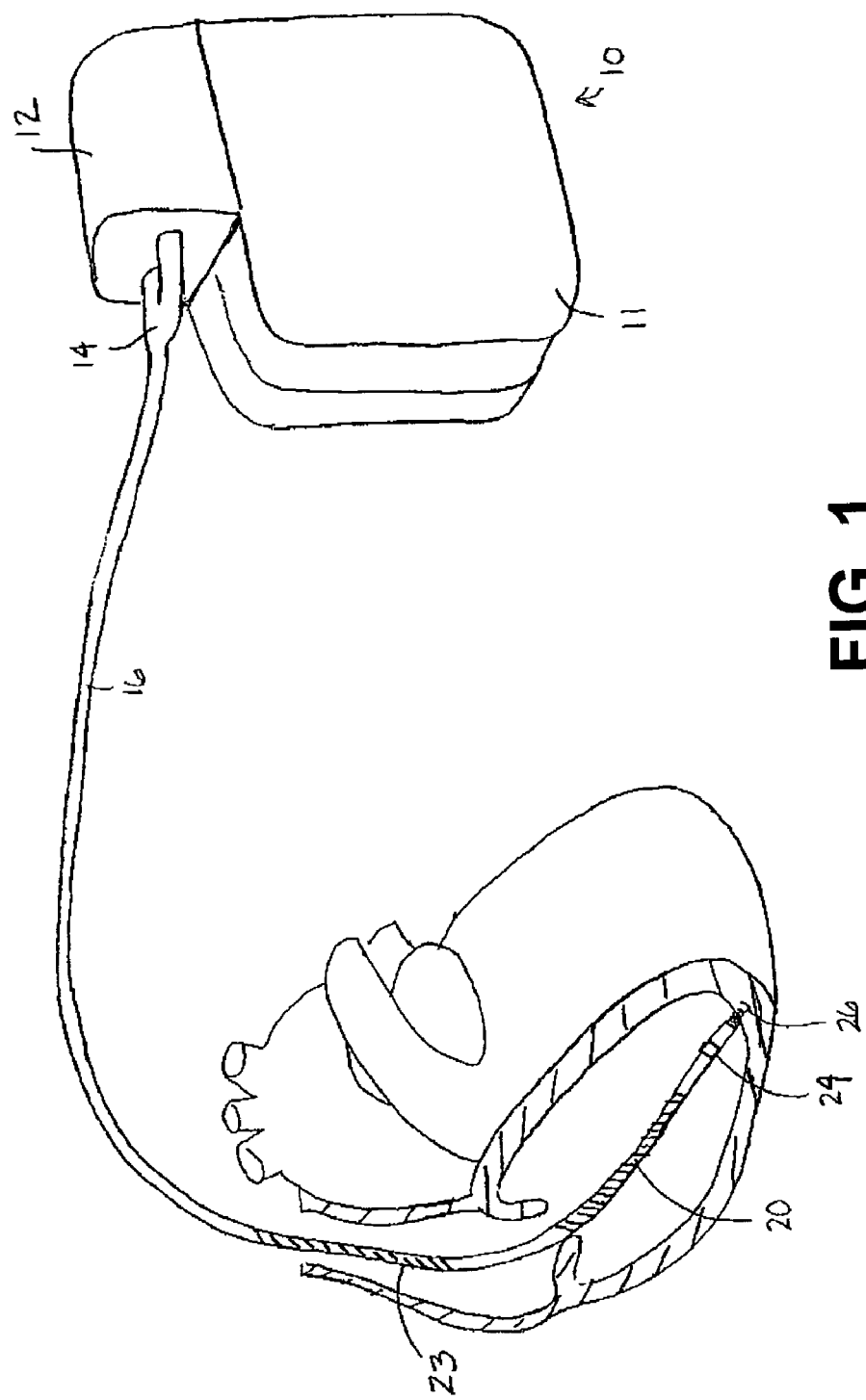
FIG. 1 is a schematic illustration of an implantable pacemaker cardioverter defibrillator (ICD), in which the present invention may be implemented, and an associated cardiac lead that is positioned in the right ventricle of a patient's heart.

The present invention is directed at providing a cardiac pacing device and method for automatically selecting an optimal evoked response sensing electrode pair and associated sensing threshold for reliable capture verification. The present invention may be implemented in single chamber, dual chamber, or multi-chamber cardiac pacing devices, which may include cardioversion and defibrillation capabilities. FIG. 1 is a schematic illustration of an implantable pacemaker cardioverter defibrillator (ICD), in which the present invention may be implemented, and an associated cardiac lead that is positioned in the right ventricle of a patient's heart. For the sake of simplicity, a single chamber device is shown, however it is recognized that the methods included in the present invention may be expanded to dual chamber and multichamber devices.

In FIG. 1, a connector block 12 receives the proximal end of a right ventricular lead 16 used for positioning electrodes for sensing right ventricular cardiac signals and delivering pacing or shocking pulses in the right ventricle. For these purposes, right ventricular lead 16 is equipped with a ring electrode 24, a tip electrode 26, a right ventricular coil electrode 20 and a superior vena cava (SVC) coil electrode 23, each of which are connected to an insulated conductor within the body of lead 16. The proximal end of the insulated conductors are coupled to corresponding connectors carried by bifurcated connector 14 at the proximal end of lead 16 for providing electrical connection to the ICD 10.

The electrodes 24 and 26 may be used for cardiac pacing as a bipolar pair, commonly referred to as a "tip-to-ring" configuration, or tip electrode 26 may be used in a unipolar configuration with the device housing 11 serving as the indifferent electrode, commonly referred to as the "can" or "case" electrode. Housing 11 may also serve as a subcutaneous defibrillation electrode in combination with one or both of the defibrillation coil electrodes 20 or 23 for delivering cardioversion shocks. In a preferred embodiment of the present invention, electrodes 24, 26, 20, 23 and housing 11 may be selected in any bipolar or unipolar sensing arrangement for sensing evoked responses following the delivery of a pacing pulse. It is recognized that alternative cardiac lead systems may be used in place of the quadrapolar lead shown in FIG. 1. Alternative lead systems may include one or more unipolar, bipolar or multipolar leads positioned for sensing and stimulating in any or all of the four heart chambers, depending on the type of device with which the lead system is used.

Figure 2:
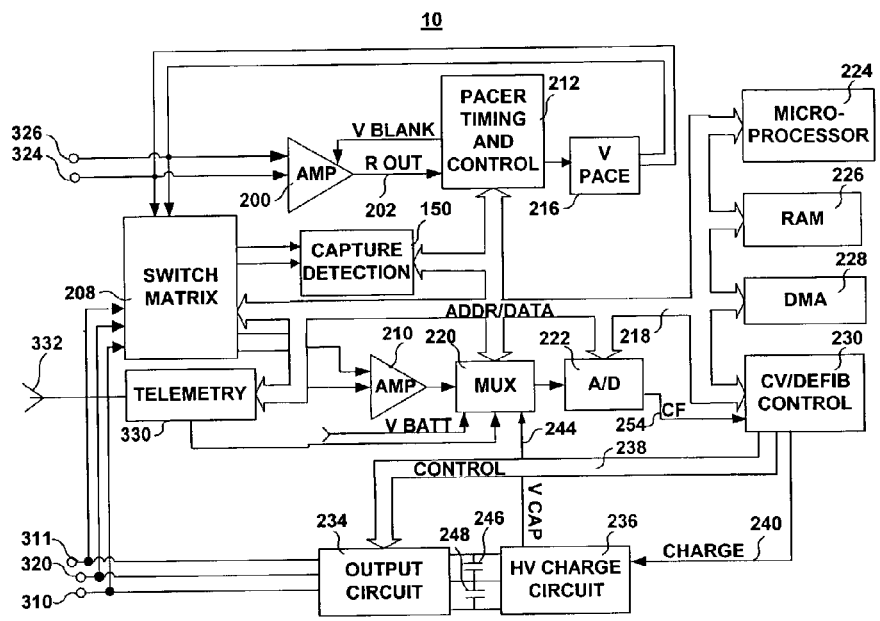
FIG. 2 is a functional block diagram of the ICD of FIG. 1.

A functional block diagram of the ICD 10 of FIG. 1 is shown in FIG. 2. This diagram should be taken as exemplary of the type of device with which the invention may be embodied and not as limiting. The disclosed embodiment shown in FIG. 2 is a microprocessor-controlled device, but the methods of the present invention may also be practiced with other types of devices such as those employing dedicated digital circuitry and/or analog circuitry.

With regard to the electrode system illustrated in FIG. 1, the ICD 10 is provided with a number of connection terminals for achieving electrical connection to cardiac lead 16. The connection terminal 311 provides electrical connection to the housing 11 for use as the indifferent electrode during unipolar stimulation or sensing. The connection terminals 320 and 310 provide electrical connection to coil electrodes 20 and 23 respectively. Each of these connection terminals 311, 320, and 310 are coupled to the high voltage output circuit 234 to facilitate the delivery of high energy shocking pulses to the heart using one or both of the coil electrodes 20 and 23 and optionally the housing 11.

The connection terminals 326 and 324 provide electrical connection to tip electrode 26 and ring electrode 24. Terminals 326 and 324 are coupled to sense amplifier 200 for sensing intrinsic cardiac signals. The sense amplifier 200 preferably takes the form of automatic gain controlled amplifiers with adjustable sensing thresholds. The general operation of the sense amplifier 200 may correspond to that disclosed in U.S. Pat. No. 5,117,824, by Keimel, et al., incorporated herein by reference in its entirety. Whenever a signal received by the sense amplifier 200 exceeds a ventricular sensing threshold, a signal is generated on the R-out signal line 202.

In accordance with the present invention, each of the connection terminals 311, 310, 320, 324 and 326 are further coupled to switch matrix 208 to allow any of housing 11, RV coil electrode 20, SVC coil electrode 23, tip electrode 26 and/or ring electrode 24 to be selectively connected to capture detection circuit 150 for use in sensing evoked responses for capture verification. Capture detection circuit 150 may also include automatic gain controlled amplifiers.

As will be described in greater detail below, a control program, executed by microprocessor 224, for optimizing the evoked response sensing vector employs capture detection circuit 150 for detecting signal characteristics used in evaluating the evoked response signal quality. An optimal evoked response sensing vector is identified based on signal quality parameters determined from the detected signal characteristics.

Switch matrix 208 is also used to select which of the available electrodes are coupled to a wide band amplifier 210 for use in digital analysis of sensed, intrinsic cardiac signals. Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known in the art.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit 330 are provided by microprocessor 224 via address/data bus 218. Received telemetry is provided to microprocessor 224 via multiplexer 220. Numerous types of telemetry systems known for use in implantable devices may be used.

In accordance with the present invention, messages for display on an external programming device may be generated by microprocessor 224 and uplinked to the programmer via telemetry circuit 330 in order to communicate results of automatic evoked response sensing vector optimization methods. As will be described in greater detail below, electrode optimization methods may determine that capture verification or pacing threshold search results are unreliable due to poor evoked response signal quality. Such information may be displayed in messages to a medical attendant on an external programmer and may include recommendations regarding the programming of automatic capture verification operations.

The remainder of the circuitry illustrated in FIG. 2 includes circuitry dedicated to providing cardiac pacing, cardioversion and defibrillation therapies. The pacer timing and control circuitry 212 includes programmable digital counters which control the basic time intervals associated with various pacing modes or anti-tachycardia pacing therapies delivered in the ventricles. Pacer circuitry 212 also determines the amplitude of the cardiac pacing pulses under the control of microprocessor 224.

During pacing, escape interval counters within pacer timing and control circuitry 212 are reset upon sensing of R-waves as indicated by signals on line 202. In accordance with the selected mode of pacing, pacing pulses are generated by ventricular pacer output circuit 216. The pacer output circuit 216 is coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves can be used to measure R—R intervals for detecting the occurrence of a variety of arrhythmias.

The microprocessor 224 includes associated ROM in which stored programs controlling the operation of the microprocessor 224 reside. A portion of the random access memory 226 may be configured as a number of recirculating buffers capable of holding a series of measured intervals for analysis by the microprocessor 224 for predicting or diagnosing an arrhythmia. In response to the detection of tachycardia, anti-tachycardia pacing therapy can be delivered by loading a regimen from microcontroller 224 into the pacer timing and control circuitry 212 according to the type of tachycardia detected.

In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors 246 and 248 is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by high voltage output circuit 234 via a control bus 238. The output circuit 234 determines the electrodes used for delivering the cardioversion or defibrillation pulse and the pulse wave shape.

Figure 3:
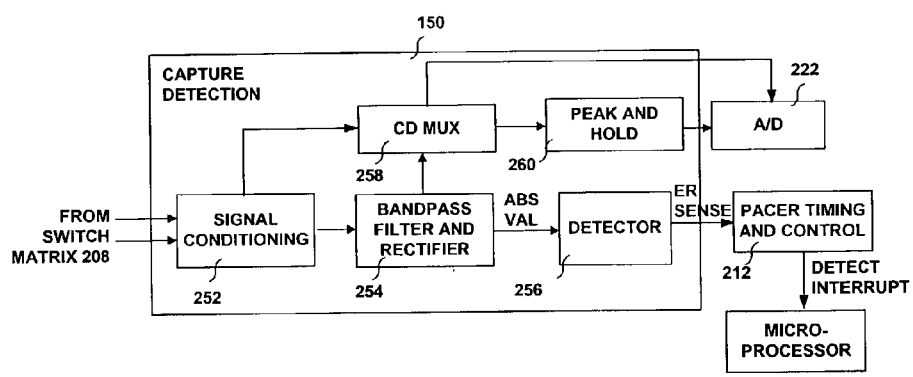
FIG. 3 is a block diagram of circuitry included in capture detection circuit 150 shown in the ICD of FIG. 2.

FIG. 3 is a block diagram of circuitry included in capture detection circuit 150 shown in device 10 of FIG. 2. Sensing input is received by signal conditioning circuitry 252 from switch matrix 208, which has selected a desired evoked response sensing vector. Signal conditioning circuitry 252 may include a preamplifier and peak tracking circuitry. Output from signal conditioning circuitry 252 is received by bandpass filter and rectifier 254, which rectifies and filters the sensed signal, preferably with a bandpass frequency range of approximately 20 to 70 Hz.

An evoked response detector circuit 256 receives the absolute value of the filtered and amplified signal and determines if capture is detected by comparing the signal to an evoked response sensing threshold. If the signal exceeds the sensing threshold, an evoked response sense signal (ER sense) is sent to pacer timing and control 212 which uses this information in controlling general pacing operations. Pacer timing and control may continue to deliver pacing as needed at the programmed pacing pulse energy as long as capture is detected. If pacer timing and control 212 does not receive an ER sense signal from capture detection circuit 150 following delivery of a pacing pulse, a back-up pacing pulse of higher energy may be delivered or pacing threshold search may be initiated.

During a pacing threshold search, an ER sense signal from capture detection circuit 150, causes pacer timing and control to generate an interrupt signal, which, in turn, causes microprocessor 224 to issue a time stamp indicating the time at which a capture detection was made. Clock cycles counted beginning from test pulse delivery to the time of evoked response detection preferably provide a time resolution on the order of 1.25 ms. As will be described in greater detail below, the time of evoked response detection may be used in validating a detection.

A capture detect multiplexer (CD MUX) 258 receives signals from signal conditioning circuitry 252 and from bandpass filter and rectifier 254. A peak track and hold circuit 260 receives the output from multiplexer 258 and delivers peak amplitude signal information to A/D converter 222 at the end of a capture detection window set by pacer timing and control 212. A/D converter 222 also receives input directly from multiplexer 258 to allow digitization of signals sensed during capture detection windows for analysis of other capture or loss of capture signal characteristics or signal morphologies.

The present invention thus provides analog circuitry for determining signal characteristics, preferably peak amplitudes, which may then be digitized for use in evaluating evoked response signal quality. Output from bandpass and rectifier circuit 254 may additionally be received by A/D converter 222 for digital determination of other signal characteristics such as slope, signal width, signal integral, signal morphology, etc. for use in evaluating evoked response signal quality.

Figure 4A:
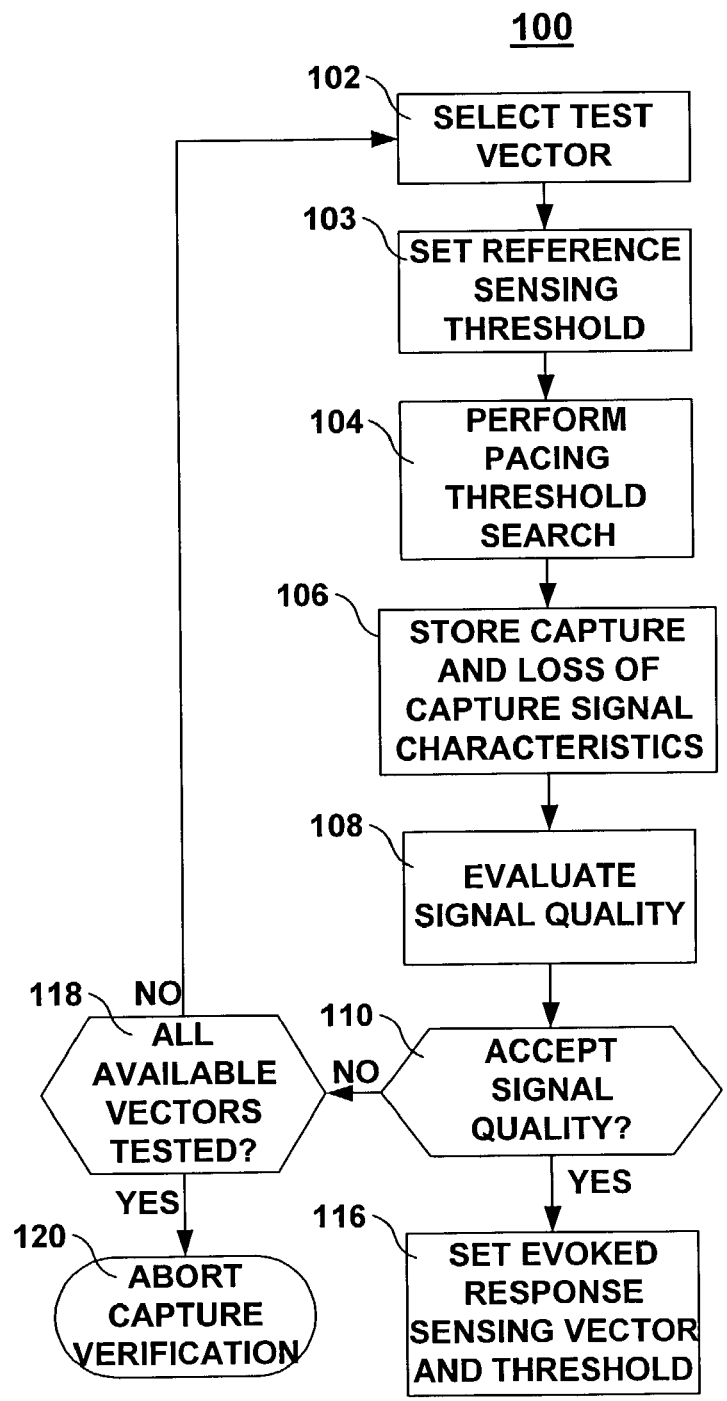
FIG. 4A is a flow chart providing an overview of a method for selecting an optimal electrode sensing vector to be used for sensing evoked responses during capture verification according to one embodiment of the present invention.

FIG. 4A is a flow chart providing an overview of a method 100 for selecting an optimal electrode sensing vector to be used for sensing evoked responses during capture verification according to one embodiment of the present invention. Method 100 is performed whenever a pacing threshold search is executed. A pacing threshold search may be performed upon detecting loss of capture, on a periodic basis, or after receiving a manual command from an external programmer.

At step 102, a test sensing vector is selected. The test vector may be a default evoked response (ER) sensing electrode pair. In regard to the electrode arrangement of FIG. 1, a default ER sensing electrode pair may be, for example, the tip electrode 26 and ring electrode 24 bipolar pair. A reference ER sensing threshold is set at step 103. This reference sensing threshold will be the threshold used for detecting capture following a test pulse. The reference sensing threshold may be a default, factory-set threshold.

At step 104, a sequence of test pacing pulses are delivered to the heart using the designated pacing electrode configuration. The test pacing pulses may be delivered according to a pacing threshold search algorithm, which may begin with a pulse having a high, suprathreshold pulse amplitude and width followed by pulses having step-wise decreasing pulse amplitude or pulse width until capture is lost. At step 106, the selected test vector is used to sense the signal following each test pulse during the pacing threshold search, and desired signal characteristics are determined by capture detection circuit 150 and stored in memory 226. The determined signal characteristics are used by microprocessor 224 in evaluating the evoked response signal quality at step 108. If the signal quality is acceptable, as determined at step 110, the pacing threshold determined during the pacing threshold search is considered valid. At step 116, the test sensing vector is set as the ER sensing vector to be used during automatic capture verification operations, and the reference sensing threshold is set as the ER sensing threshold.

If the signal quality is not acceptable at step 110, the method 100 determines if all available sensing vectors have been tested at step 118. If not, a new test vector is selected at step 102 and the method 100 is repeated. If all available sensing vectors have been tested, then automatic capture verification is deemed unreliable for the available sensing vectors and is aborted at termination step 120. A message may be generated for display on an external programming device indicating that the pacing threshold results of the pacing threshold search are considered invalid, and disabling capture verification is recommended.

In cardiac pacing systems employing a lead system that provides only one possible evoked response sensing vector, the method of FIG. 4A may still be applied to validate the sensing vector as being reliable for capture detection. If the sensing vector does not meet the signal quality requirements, disabling automatic capture verification may be recommended.

Figure 4B:
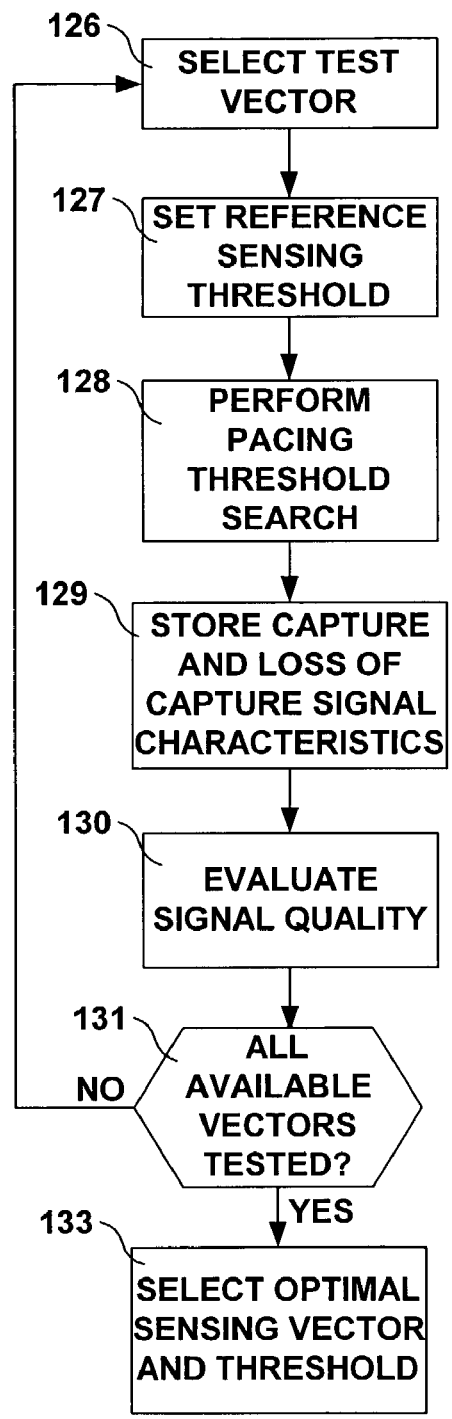
FIG. 4B is a flow chart providing an overview of an alternative method 125 for automatically selecting an optimal ER sensing vector.

FIG. 4B is a flow chart providing an overview of an alternative method 125 for automatically selecting an optimal ER sensing vector. Generally, method 100 described above selects a test sensing vector and, if the test vector meets predetermined signal quality requirements, the test vector may be accepted as the ER sensing vector. If the signal requirements are not met, other available sensing vectors are tested sequentially until an acceptable ER sensing vector is found. Method 125 of FIG. 4B first tests all available test sensing vectors and then selects the optimal ER sensing vector based on the evaluation of the ER signal quality of all available sensing vectors.

At steps 126 and 127 of method 125, a test sensing vector is selected and a reference sensing threshold is set. The signal sensed using the test vector following each pulse in a pacing threshold search, initiated at step 128, is characterized at step 129, and signal characteristics for both capture signals and loss of capture signals are stored in memory 226. Based on the stored signal characteristics, the signal quality is evaluated for the test vector at step 130. Steps 126 through 130 are then repeated for all available sensing vectors until all available vectors have been tested, as determined at decision step 131. The test vector having the best signal quality, based on predetermined optimization criteria, is selected at step 133 as the ER sensing vector and the ER sensing threshold is set accordingly.

Figure 5:
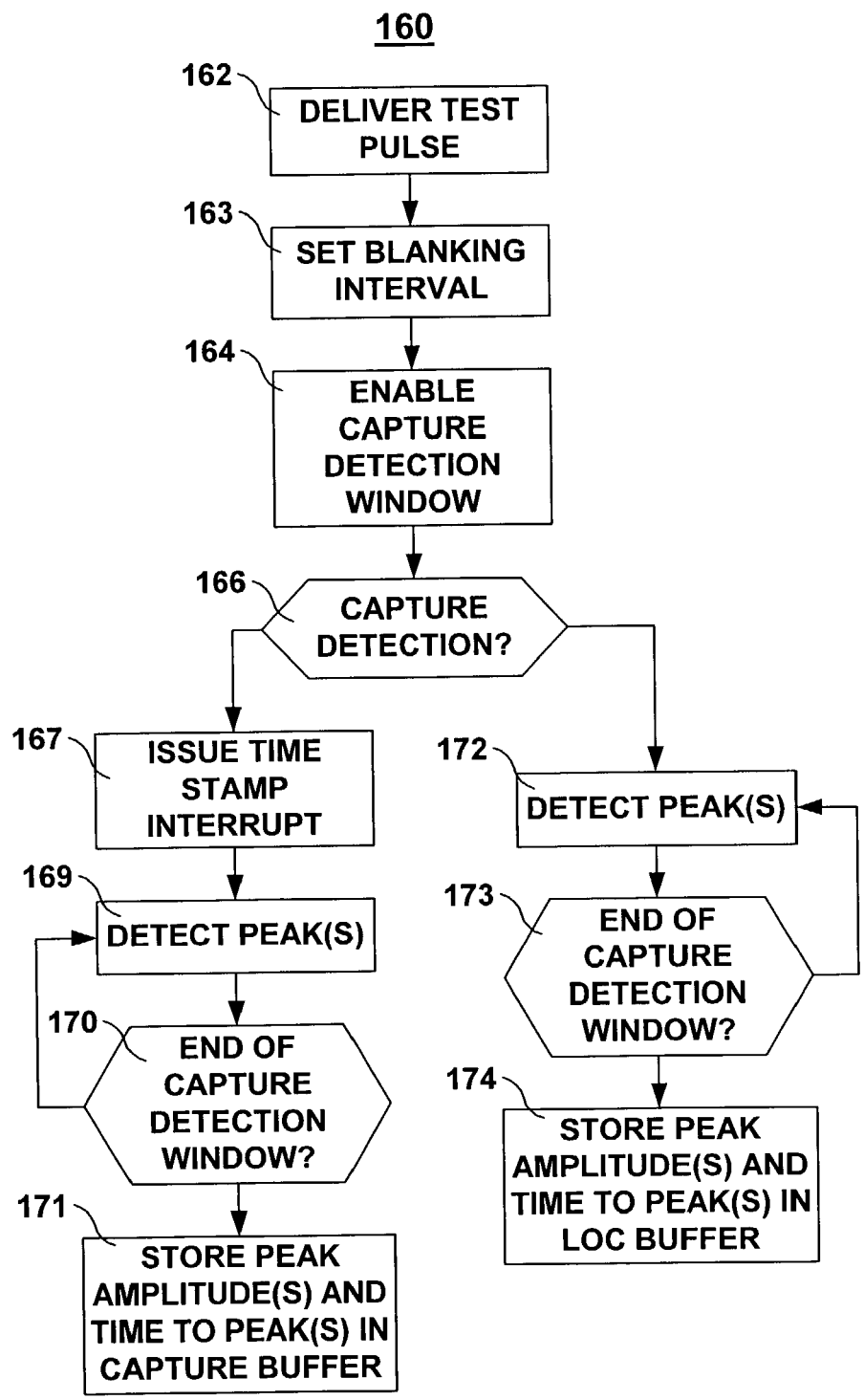
FIG. 5 is a flow chart summarizing a method for characterizing a capture or loss of capture signal sensed following the delivery of a pacing threshold search test pulse according to one embodiment of the present invention.

FIG. 5 is a flow chart summarizing a method for characterizing a capture or loss of capture signal sensed following the delivery of a pacing threshold search test pulse according to one embodiment of the present invention. The method 160 for determining and storing capture and loss of capture (LOC) signal characteristics may be used by methods 100 or 125 shown in FIGS. 4A and 4B. Preferably method 160 includes the determination of capture and LOC signal characteristics that allow at least an evoked response signal-to-noise ratio and an evoked response sensing margin to be determined. Methods for determining an evoked response signal-to-noise ratio and sensing margin will be described in greater detail below.

In signal characterization method 160, a test pulse included in a pacing threshold search is delivered at step 162, using designated pacing electrodes. At step 163, a blanking interval is set immediately following the test pulse to prevent saturation of the sense amplifier included in capture detection circuit 150 due to polarization artifact. At step 164, a capture detection window is enabled during which a signal is sensed by the test sensing vector. The capture detection window is enabled following the test pulse and blanking interval and extends a predetermined time interval after the test pulse, during which an evoked response is expected to occur when the test pulse energy is greater than the capture threshold. A capture detection window is typically on the order of 110 ms.

Figure 6:
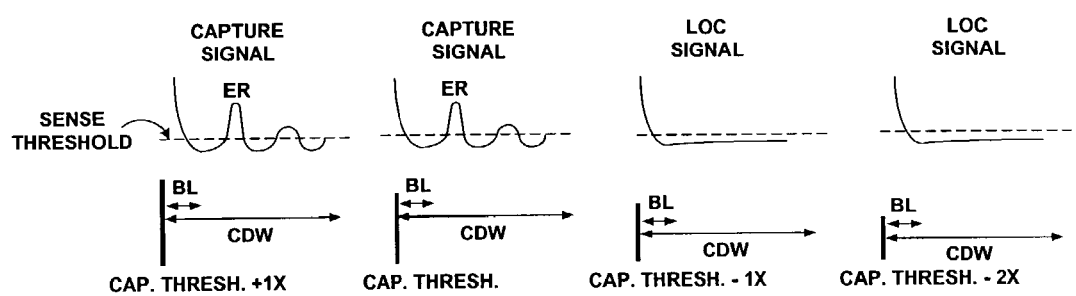
FIG. 6 is an illustration of a set of test pulses that may be included in a test sequence and the associated sensed signals following each test pulse.

FIG. 6 is an illustration of a set of test pulses that may be included in a test sequence and the associated sensed signals following each test pulse. Reliable capture verification depends on the ability of device 10 to differentiate between a loss of capture (LOC) signal and a capture signal. Therefore, the capture and LOC signals that are characterized for ER sensing vector optimization preferably include signals associated with test pulses equal to or slightly greater than the pacing threshold and test pulses just below the pacing threshold. The contribution of the polarization artifact to the sensed signals will be similar with the primary difference in the sensed signal being the presence of an evoked response in the signals associated with suprathreshold test pulses. Therefore signals that are characterized during method 160 of FIG. 5 may be associated with a test pulse at the capture threshold (CAP. THRESH.); a test pulse at the capture threshold plus a predetermined step change (X) in pulse width or pulse amplitude (CAP. THRESH.+1X); a test pulse at the capture threshold minus a step change in pulse width or amplitude (CAP. THRESH.−1X); and a test pulse at the capture threshold minus twice the step change in pulse width or pulse amplitude (CAP. THRESH.−2X). The step change (X) in pulse width or pulse amplitude may be the smallest increment available in device 10, which may typically be on the order of 0.1 ms or 0.125 Volts. Each test pulse is followed by a blanking interval (BL) and a capture detection window (CDW) as set by pacer timing and control 212. During general capture verification operations, if the sensed signal exceeds a sensing threshold during the capture detection window, an evoked response (ER) is detected confirming capture.

In method 160 of FIG. 5, if a capture detection is made at step 166 following a pacing threshold search pulse, an interrupt signal is generated by pacer timing and control 212 at step 167 so that a time stamp may be stored in memory 226 indicating the time after the test pulse at which capture detection was made. At step 169, signal peaks are detected by sense amplifier and peak track and hold circuit 260 of capture detection circuit 150. One or more peak amplitudes of the sensed signal may be detected. Peak detection continues until the capture detection window expires as determined at decision step 170. At the end of the capture detection window, an end interrupt signal is generated by pacer timing and control circuit 212, and the capture detection result (capture) and peak amplitude information are available from A/D converter 222. The peak amplitude(s), and optionally the time at which they occur following the test pulse, are stored in a memory buffer designated for capture signal data at step 170. Preferably at least one peak amplitude is determined for at least two test pulses that result in capture and have a pulse energy at or near the pacing threshold, as generally shown in FIG. 6.

If capture is not detected at step 166, the peak amplitude (s) of the LOC signal are detected by peak track and hold circuit 260 at step 172. Upon expiration of the capture detection window, as determined at decision step 173, the peak amplitude(s), and optionally the time at which they occur following the test pulse, are stored in a memory buffer designated for LOC signal data at step 174. Preferably, LOC signal data are stored for at least two test pulses that result in loss of capture and are near the pacing threshold as generally shown in FIG. 6.

Figure 7:
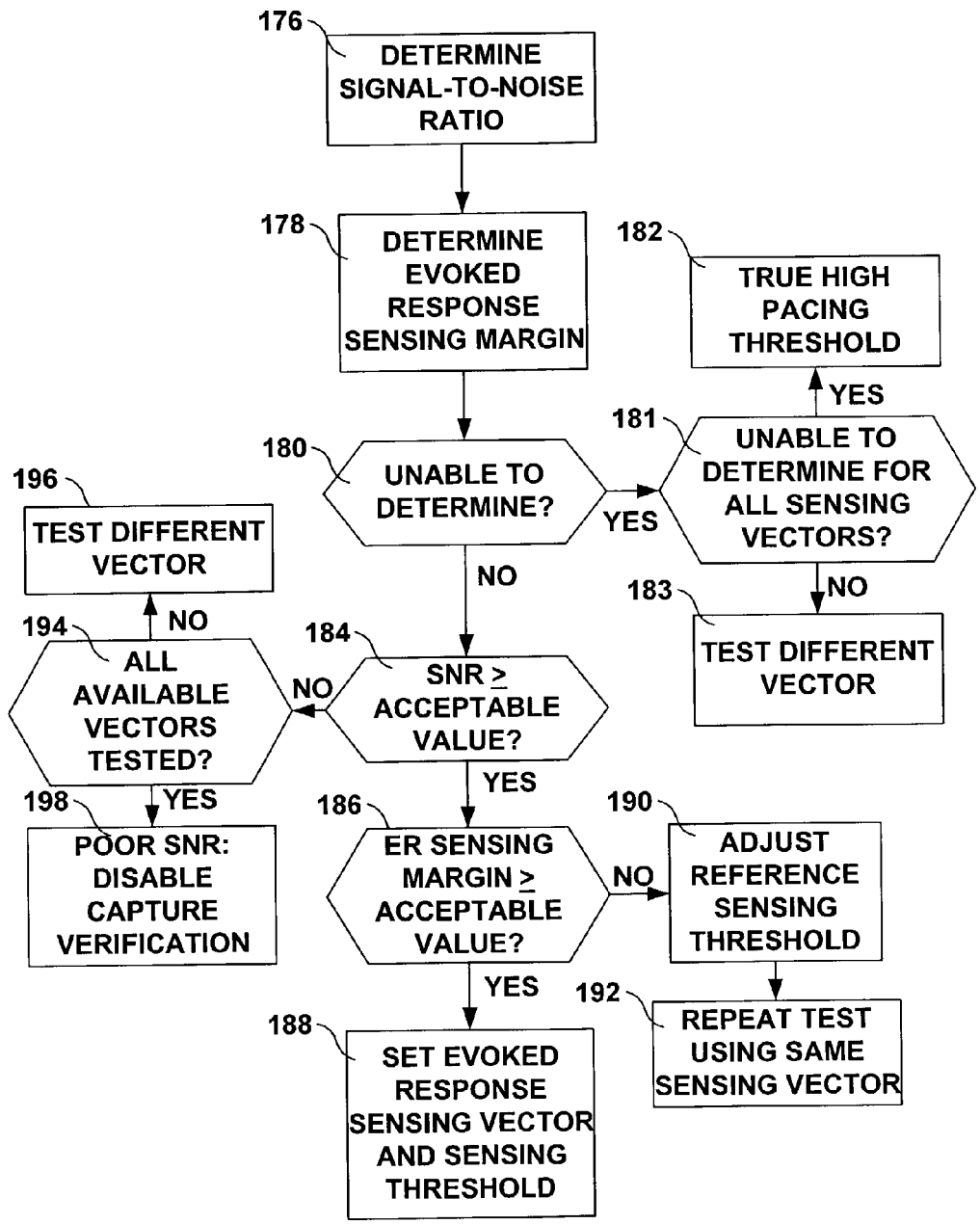
FIG. 7 is a flow chart summarizing steps performed in one embodiment for evaluating the ER signal quality and selecting an optimal ER sensing vector.

In accordance with the present invention, the stored peak amplitudes, and optionally the capture detection time and peak amplitude times, are then available for evaluating the ER signal quality. FIG. 7 is a flow chart summarizing steps performed in one embodiment for evaluating the ER signal quality and selecting an optimal ER sensing vector. Based on the signal characterization performed according to method 160 of FIG. 5, an evoked response signal-to-noise ratio is determined at step 176, and an evoked response sensing margin is determined at step 178.

Figure 8:
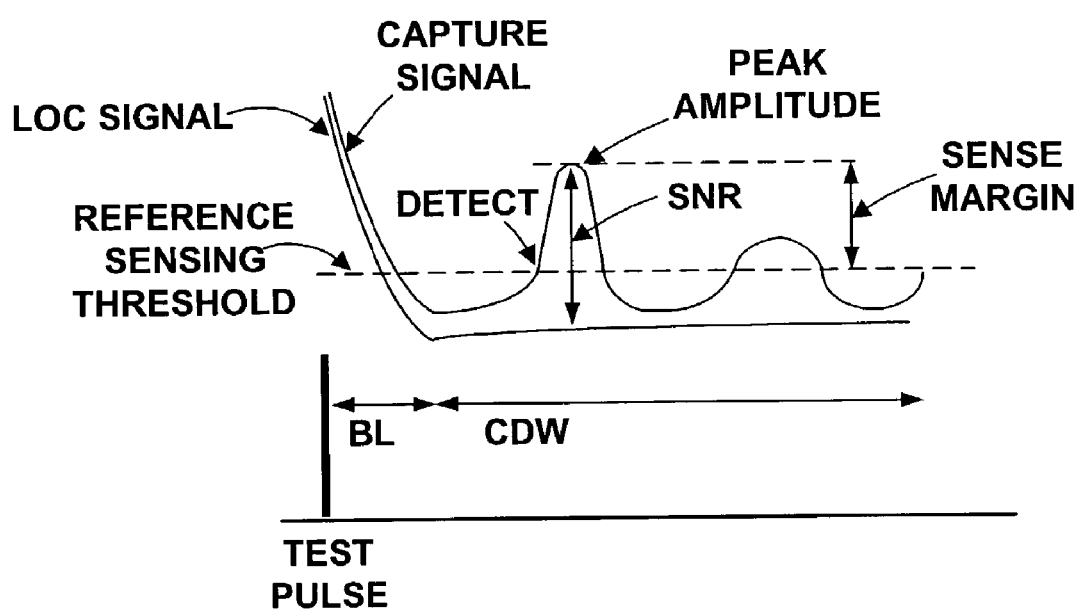
FIG. 8 is an illustration of a sensed capture signal and loss of capture signal depicting how an ER signal-to-noise ratio and ER sensing margin may be determined.

FIG. 8 is an illustration of a sensed capture signal and loss of capture signal depicting how an ER signal-to-noise ratio and ER sensing margin may be determined. The ER signal-to-noise ratio (SNR) is the ratio of the peak amplitude of a capture signal and the peak amplitude of a loss of capture (LOC) signal detected during a capture detection window. Preferably, the ER SNR is calculated using the lowest peak amplitude detected and stored in the capture memory buffer and the highest peak amplitude detected and stored in the LOC memory buffer, as given by Equation 1:

$$ER\ SNR = \frac{\text{Min}(CAP_{peak})}{\text{Max}(LOC_{peak})}$$

The ER sensing margin may be defined as the ratio of the peak amplitude of a capture signal and the reference sensing threshold. Preferably the ER sensing margin is calculated using the lowest peak amplitude stored in the capture memory buffer, as given by Equation 2:

$$ER\ \text{Sensing Margin} = \frac{\text{Min}(CAP_{peak})}{\text{Threshold}}. \quad (2)$$

If the ER SNR and the ER sensing margin are indeterminable, as indicated at decision step 180 of FIG. 7, a true high pacing threshold is suspected. The SNR and ER sensing margin will be indeterminable if no capture detection is made following any test pulse, even a maximum amplitude or maximum pulse width test pulse. Remaining available sensing vectors should be tested to verify that the persistent LOC detection is not due to ER undersensing associated with a particular sensing vector. If all sensing vectors have not yet been tested, as determined at step 181, a different test vector is selected at step 183 and a pacing threshold search is repeated.

If the SNR and ER sensing margin are indeterminable for all available sensing vectors, as determined at step 181, an elevated pacing threshold is confirmed at step 182. A highly elevated pacing threshold may be due to lead dislodgment, lead fracture, a change in medical therapy or other condition. Intervention may be required to resolve the problem, therefore, a message indicating a high pacing threshold may be generated at step 182 for display on an external programmer to alert a medical attendant of the condition.

When the SNR and ER sensing margin are determined for a given test sensing vector, the ER SNR is compared to a predefined acceptable value at decision step 184. For reliable capture detection, the peak amplitude of a capture signal should generally be several times greater than a peak amplitude of a loss of capture signal to allow easy discrimination between capture and LOC. Therefore, the SNR, as determined according to Equation 1 above, is preferably greater than 2, more preferably greater than 4. If the SNR is not greater than the predefined acceptable value, an alternate sensing vector may be selected for testing at step 196, if all available sensing vectors have not yet been tested as determined at decision step 194. If all available sensing vectors have already been tested, the evoked response sensing vector optimization method is terminated at step 198 due to poor SNR. A message may be generated at step 198 indicating to a clinician that disabling of automatic capture verification is recommended due to poor SNR.

If the SNR is determined to be acceptable at decision step 184, the ER sensing margin is compared to a predefined acceptable value at decision step 186. The ER sensing margin is preferably large enough that marginal evoked response sensing is avoided. Marginal evoked response sensing occurs when the peak ER amplitude is nearly equal to the sensing threshold causing some evoked responses to be detected and some not detected. Marginal evoked response sensing can result in false LOC detection, possibly triggering unnecessary back-up pacing pulses or pacing threshold searches. To avoid marginal evoked response sensing, an ER sensing margin calculated according to Equation 2 preferably exceeds a predetermined minimum, which may be on the order of 1.25.

If the ER sensing margin is not acceptable at decision step 186, the reference sensing threshold may be made more sensitive (adjusted to a lower numeric value) at step 190. At step 192, a pacing threshold search is repeated using the same sensing vector to re-determine the SNR and ER sensing margin using the new reference sensing threshold. If the ER sensing margin is found to be acceptable, the pacing threshold result of the pacing threshold search is deemed reliable. At step 188, the test sensing vector may be automatically programmed as the ER sensing vector, and the adjusted reference sensing threshold may be automatically programmed as the ER sensing threshold for use during automatic capture verification operations.

Figure 9:
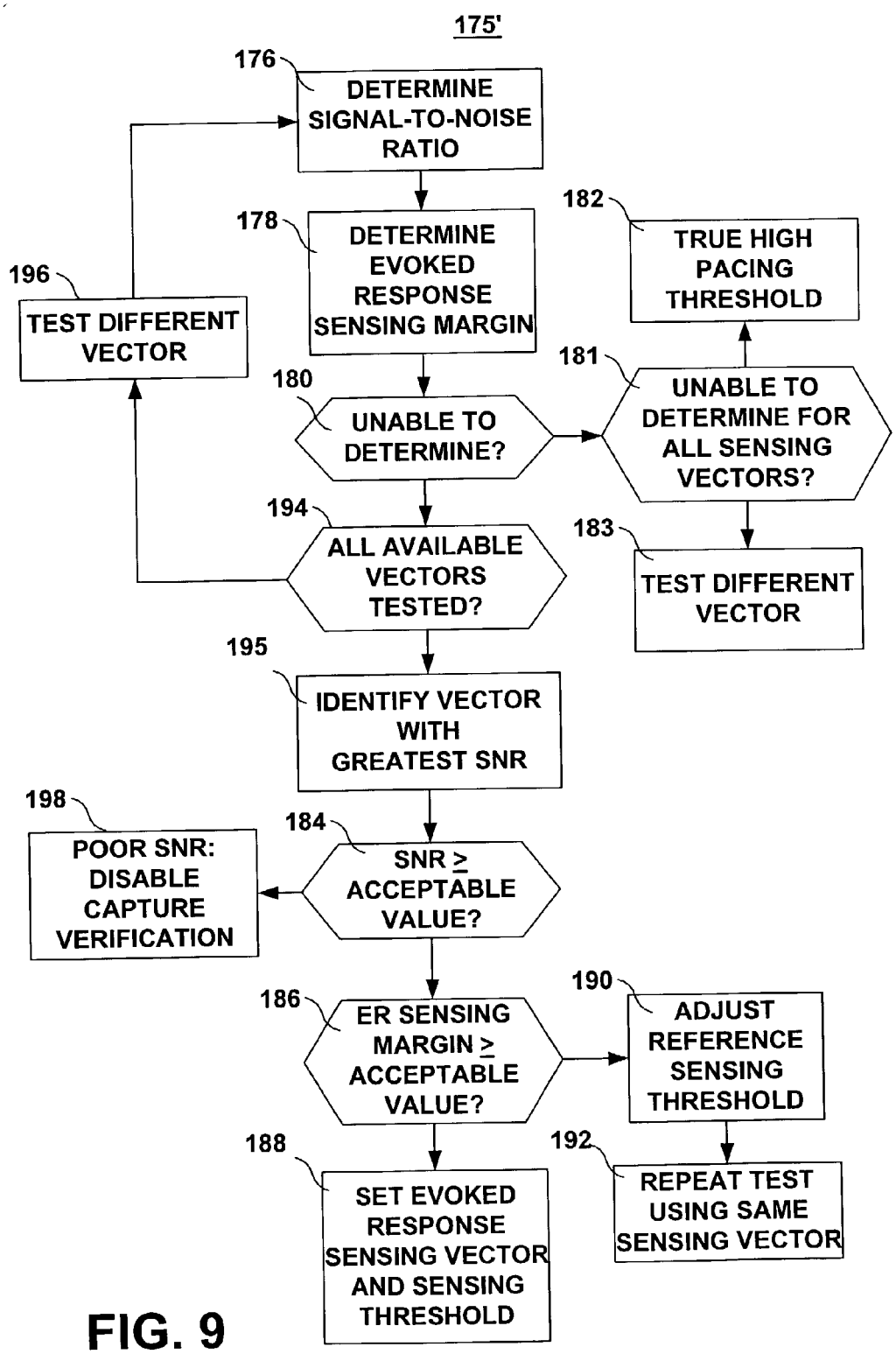
FIG. 9 is a flow chart summarizing the steps included in an alternative method for selecting an optimal evoked response sensing vector based on the signal quality evaluated from all available sensing vectors.

FIG. 9 is a flow chart summarizing the steps included in an alternative method for selecting an optimal evoked response sensing vector based on the signal quality evaluated from all available sensing vectors. Identically numbered steps in FIG. 9 correspond to those in FIG. 7. The method 175' of FIG. 9 begins by determining the SNR and ER sensing margin at steps 176 and 178 as described above.

If the SNR and ER sensing margin are indeterminable, at step 180, a true high pacing threshold is suspected, and method 175' follows steps 181, 182, and 183 accordingly, as described previously.

If the SNR and ER sensing margin are determined for a given test sensing vector, the method of FIG. 9 proceeds to test all available sensing vectors before selecting an optimal ER sensing vector. Therefore at step 194, if all available vectors have not been tested, a different vector is selected at step 196 and the pacing threshold search and signal characterization is repeated so that the SNR and ER sensing margin may be determined for all available vectors.

Once all available vectors have been tested, the vector associated with the highest SNR is identified at step 195. If the highest SNR is not greater than a predefined acceptable value, as determined at decision step 184, then the pacing threshold result of the pacing threshold search is deemed unreliable, and disabling automatic capture verification is recommended at step 198 due to poor SNR.

If the highest SNR is acceptable at step 184, the ER sensing margin for the same sensing vector is compared to a predefined acceptable value at decision step 186. If the ER sensing margin is acceptable, the pacing threshold search result is deemed reliable, and automatic capture verification may be recommended. The evoked response sensing vector and sensing threshold for capture verification operations may be automatically programmed at step 188 to be the test vector resulting in the highest SNR and the corresponding reference sensing threshold. If the ER sensing margin is not acceptable, the reference sensing threshold may be adjusted at step 190 and the pacing threshold search may be repeated at step 192, as described previously. Alternatively, the sensing vector having the next highest SNR may be selected if the SNR exceeds a predetermined minimum and the ER sensing margin is acceptable.

Figure 10:
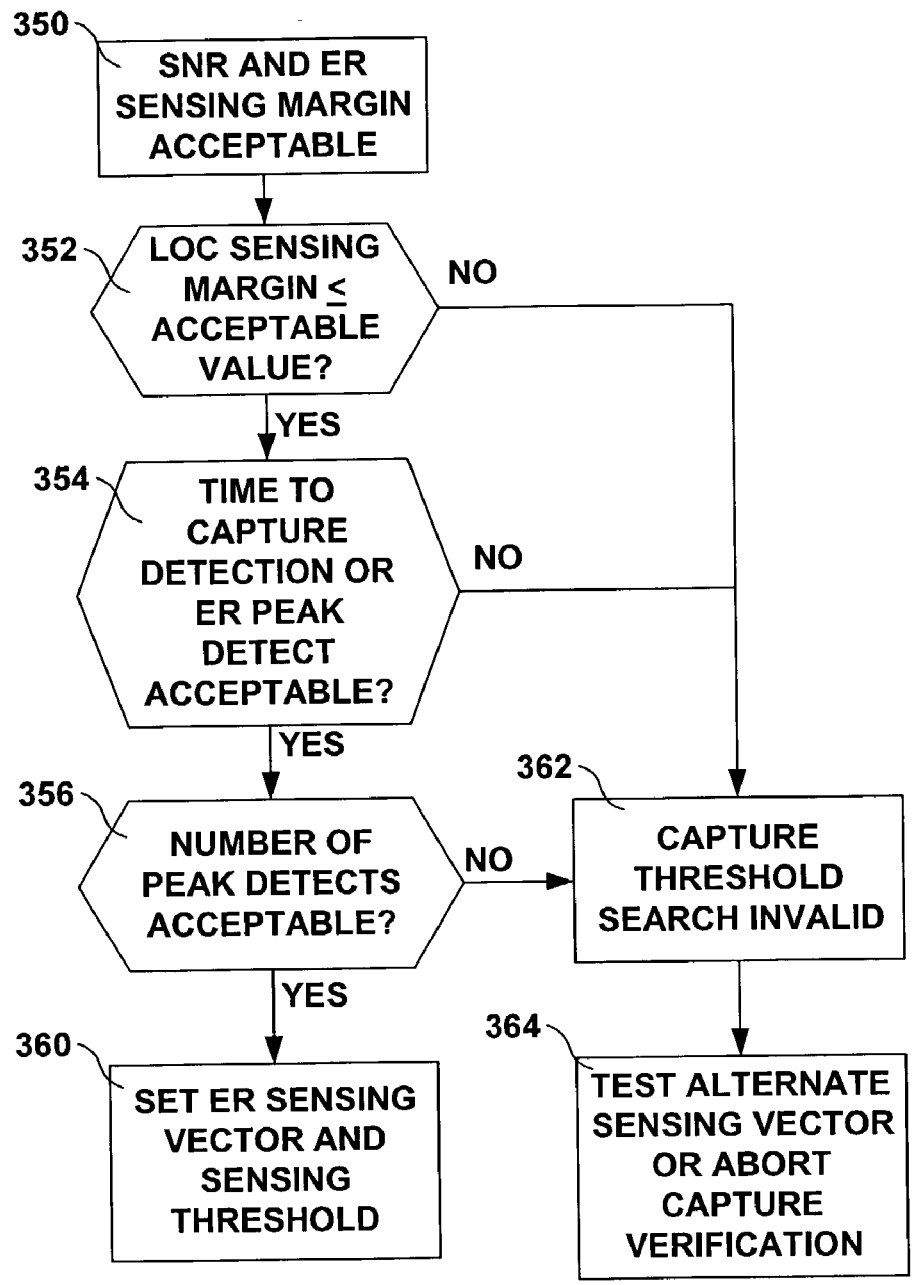
FIG. 10 is a flow chart summarizing additional steps that may be included in the methods of FIG. 7 or 9 for selecting an optimal ER sensing vector.

FIG. 10 is a flow chart summarizing additional steps that may be included in the methods of FIGS. 7 or 9 for selecting an optimal ER sensing vector. After identifying a sensing vector having an acceptable SNR and ER sensing margin using the methods of FIGS. 7 or 9, as indicated at step 350, additional signal quality criteria may be evaluated to ensure optimal evoked response sensing for reliable pacing threshold determination and capture verification.

At decision step 352, a loss of capture (LOC) sensing margin may be determined and compared to a predefined acceptable value. The LOC sensing margin may be defined as the ratio of the peak LOC signal amplitude to the reference sensing threshold. Preferably, the highest LOC peak amplitude stored in a LOC memory buffer is used in calculating a LOC sensing margin, as given by Equation 3:

$$LOC \text{ Sensing Margin} = \frac{MAX(LOC_{peak})}{\text{Threshold}}. \quad (3)$$

If the LOC signal during a capture detection window following a subthreshold test pulse is larger in amplitude than expected, e.g. because of noise, false capture detections may be made. Therefore a safe margin between the maximum amplitude of the LOC signal and ER sensing threshold is desired to prevent false capture detections. An acceptable LOC sensing margin may be on the order of 0.1, for example.

If the LOC sensing margin as calculated according to Equation (3) above is higher than a predetermined acceptable value, an alternative sensing vector may be tested at step 364 or the reference sensing threshold may be adjusted. A less sensitive sensing threshold (higher numeric value) may be selected for the same test vector and the test may be repeated.

If the LOC sensing margin is acceptable, the time at which capture detection and/or the time of a detected peak amplitude of a capture signal may be evaluated at decision step 354. If an early capture detection is made, for example within 10 ms of the end of the blanking interval, the detection may be due to a high polarization signal that has not substantially diminished such that it is interfering with evoked response sensing. An early capture detection may be suspected of being unreliable due to polarization artifact.

If a late capture detection is made, for example within 10 ms of the end of the capture detection window, an inverted slew of the sensed signal may have occurred due to over recharging of the pacing output capacitor after delivering the test pulse. Therefore, a late capture detection may be suspected of being unreliable due to capacitor over recharge.

In addition or alternatively to examining the time of capture detection to exclude early or late capture detections, the time of one or more peak amplitude detections associated with a capture signal may be examined at decision step 354. If the time of a peak amplitude detection is not consistent with prior peak amplitude detections, or is within the first or last few milliseconds of the capture detection window, the capture detection may be due to oversensing of noise resulting from electromagnetic interference, far-field cardiac signals, skeletal muscle motion, or otherwise. Therefore, the capture detection may be suspected of being unreliable due to noise. In alternative embodiments, the time and amplitude of detected peaks, and possibly other attributes, may be examined together to determine if these signal attributes are consistent. Inconsistencies may indicate a suboptimal sensing vector requiring a new pacing threshold search and vector optimization and re-determination of the associated signal attributes.

At decision step 356, the number of peaks detected from a capture signal during a capture detection window may be examined. If a large number of peaks are detected, the signal may be contaminated with noise and the capture detection may be considered unreliable. Therefore, the number of peaks detected during a capture detection window may be compared to an acceptable value to eliminate noisy signals. A characteristic frequency of an evoked response signal sensed by a given sense amplifier may be used for determining an acceptable number of peaks, for example on the order of 1 to 4 peaks. If a greater number of peaks are detected during a capture detection window, the signal is noisy. For example, if 60 Hz noise is present, on the order of 6 to 10 peaks could be detected during a capture detection window.

If any of the decision steps 352 through 356 have a negative result, the pacing threshold result of the pacing threshold search may be concluded to be invalid at step 362. An alternative sensing vector may be tested at step 364 or the reference sensing threshold may be adjusted, for example in the case of a high LOC sensing margin. If all available sensing vectors have been exhausted, disabling automatic capture verification may be recommended.

Additional signal quality criteria may be defined and evaluated based on signal characteristics determined by capture detection circuit 150 or digitized signal characteristics determined by A/D converter 222. Such signal characteristics may relate to the time or magnitude of peak amplitudes and time of detections as described above, or additionally or alternatively, relate to other signal characteristics such as signal slopes, integrals, threshold crossings, morphology or otherwise. Various signal quality criteria may therefore be defined based on ratios, differences, or other relationships between signal characteristics obtained from capture and/or LOC signals and a reference sensing threshold.

Figure 11:
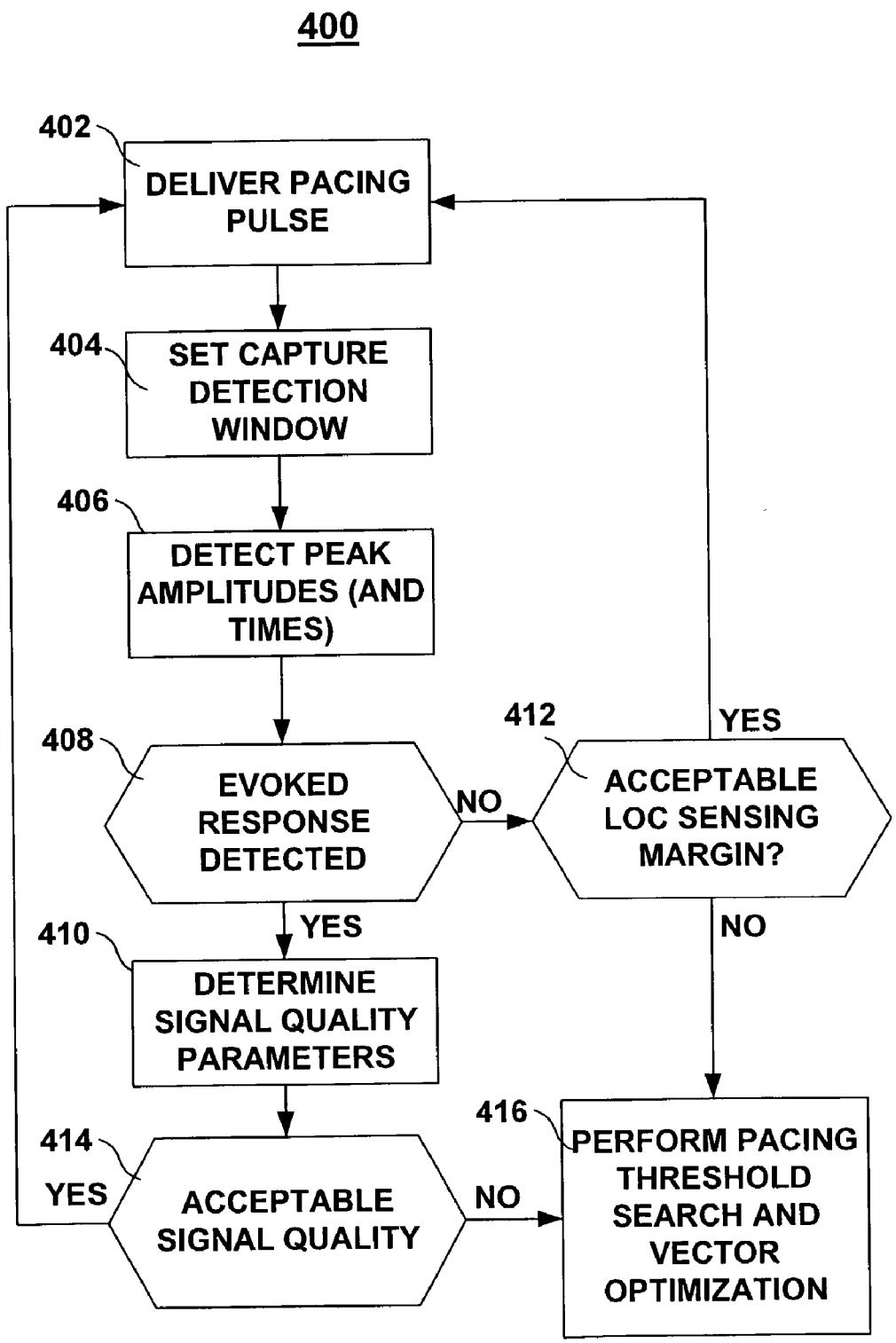
FIG. 11 is a flow chart summarizing a method for verifying evoked response signal quality during capture verification operations.

FIG. 11 is a flow chart summarizing a method for verifying evoked response signal quality during capture verification operations. Methods for determining signal quality parameters during a pacing threshold search may be adapted for use during capture verification operations to verify that signal quality remains acceptable. Verification of signal quality may be performed on a beat-by-beat basis during beat-by-beat capture verification or on a less frequent, sampled basis. If the signal quality is found to have deteriorated, a pacing threshold search and evoked response sensing vector optimization procedure, as described above, may be triggered.

At step 402, a pacing pulse is delivered in accordance with the device 10 operating mode. At step 404, a capture detection window is set, and capture detect circuit 150 detects signal peak amplitudes, and optionally peak times sensed using the most recently determined optimal evoked response sensing vector. If an evoked response is detected at step 408, based on the previously determined optimal sensing threshold, the peak amplitude detected at step 406 may be used to determine evoked response signal quality parameters at step 410.

Signal quality parameters may be determined based on the peak amplitude information detected at step 406 and loss of capture signal characteristics stored during the most recent pacing threshold search. For example, an ER SNR may be calculated as the ratio of the peak amplitude detected at step 406 and the highest loss of capture peak amplitude stored during the last pacing threshold search. An evoked response sensing margin may be calculated as the peak amplitude detected at step 406 and the current sensing threshold. Other signal characteristics used for evaluating signal quality during vector optimization methods, such as early or latent capture detections, number of peaks, etc., may also be used in determining signal quality parameters at step 410.

If the signal quality parameters meet predetermined acceptable limits, as determined at decision step 414, then beat-by-beat capture verification may continue, by returning to step 402, using the currently selected evoked response sensing vector and threshold. However, if the signal quality parameters are not acceptable, the evoked response signal sensed using the currently selected vector may have deteriorated. A pacing threshold search may be triggered at step 416 allowing a sensing vector optimization procedure to be performed to reset the evoked response sensing vector and threshold, as necessary.

If an evoked response is not detected at decision step 408, the loss of capture signal may optionally be examined for an acceptable loss of capture sensing margin at decision step 412. The peak amplitude detected at step 406 may be used to calculate a LOC sensing margin based on the currently selected sensing threshold and compared to an acceptable value at step 412. If the LOC sensing margin, calculated as the ratio of the peak amplitude detected at step 406 to the sensing threshold, is too high, a pacing threshold search and evoked response sensing vector optimization procedure may be triggered at step 416. Worsening signal quality, due to increasing noise for example, may be identified by an increase in the LOC sensing margin before false capture detections are made due to a noisy signal. Thus, signal quality parameters may be used for ongoing verification of acceptable evoked response sensing during capture verification operations.

The circuitry and associated methods provided by the present invention thus allow an ER sensing vector to be optimized based on the quality of the capture (and loss of capture) signals. Rather than only indicating that a capture or LOC detection has been made, the ER sensing vector optimization methods included in the present invention for evaluating the capture and LOC signals provides information on the ER signal quality. Based on this information, unreliable ER sensing vectors and pacing threshold measurements may be eliminated. False capture or false LOC detections may be avoided. Hence, automatic capture verification and capture threshold searches may be performed more reliably when utilizing an optimized ER sensing vector and sensing threshold.

Furthermore, it is contemplated that methods provided by the present invention for evaluating the quality of an evoked response signal may be applied to evaluating the quality of other types of sensed signals used in other sensing applications, other than evoked response sensing. Selection of optimal sensing vectors for any physiologic signal of interest may be improved by determining signal quality parameters based on identified signal characteristics and selecting an optimal sensing vector based on the signal quality parameters meeting predetermined acceptance criteria, in accordance with the methods and concepts of the present invention. The detailed descriptions of embodiments provided herein are therefore intended to illustrate the concepts of the present invention and are not to be considered limiting with regard to the following claims.

What is claimed is:

1. A method for automatically selecting evoked response sensing electrodes, comprising:
    selecting an evoked response sensing electrode pair;
    delivering a sequence of test pulses including a first set of test pulses having a first pulse energy exceeding a capture threshold and a second set of test pulses having a second pulse energy less than the capture threshold;
    setting a capture detection time window following each test pulse during which a signal is sensed using the selected evoked response sensing electrode pair;
    determining a maximum signal amplitude of the sensed signal occurring during the capture detection window following each of the test pulses included in the first set and the second set;
    determining a minimum value of the determined maximum signal amplitudes corresponding to the first set of test pulses;
    determining a signal quality parameter based on the minimum value of the maximum signal amplitudes corresponding to the first set of test pulses; and
    accepting the selected evoked response sensing electrode pair in response to the signal quality parameter.

2. The method of claim 1 wherein determining the signal quality parameter includes determining a ratio of the minimum value of the maximum signal amplitudes corresponding to the first set of test pulses and a predetermined first threshold.

3. The method of claim 2, further comprising:
    comparing the signal quality parameter to a predetermined second threshold; and
    adjusting the first threshold in response to the signal quality parameter being less than the second threshold.

4. The method of claim 1 further comprising determining a maximum value of the determined maximum signal amplitudes corresponding to the second set of test pulses.

5. The method of claim 4 wherein determining the signal quality parameter includes determining a ratio of the maximum value of the maximum signal amplitudes corresponding to the second set of test pulses and a predetermined first threshold.

6. The method of claim 5 further comprising:
comparing the signal quality parameter to a predetermined second threshold; and
adjusting the first threshold in response to the signal quality parameter being greater than the second threshold.

7. The method of claim 4 wherein determining the signal quality parameter includes determining a ratio of the minimum value of the maximum signal amplitudes corresponding to the first set of test pulses and the maximum value of the maximum signal amplitudes corresponding to the second set of test pulses.

8. The method of claim 1 wherein determining the signal quality parameter further includes determining one of:
a time corresponding to the maximum signal amplitude, and the number of signal peaks occurring during the capture detection window.

9. The method of claim 1 further comprising:
detecting capture; and
wherein determining the signal quality parameter further includes determining a capture detection time.

10. The method of claim 1 further comprising:
selecting at least one alternate sensing electrode pair,
determining a signal quality parameter for the alternate sensing electrode pair, and
selecting an optimal sensing electrode pair based on the signal quality parameter for the alternate sensing electrode pair and the signal quality parameter for the selected evoked response sensing electrode pair.

11. A system implemented in an implantable medical device, the system comprising:
means for selecting an evoked response sensing electrode pair;
a pulse generator for delivering a sequence of test pulses including a first set of test pulses having a first pulse energy exceeding a capture threshold and a second set of test pulses having a second pulse energy less than the capture threshold;
a capture detection module for receiving a signal from the selected evoked response sensing electrode pair; and
a processor for receiving a signal from the selected evoked response sensing electrode pair, determining a maximum signal amplitude of the received signal following each of the test pulses included in the first set and the second set, determining a minimum value of the determined maximum signal amplitudes corresponding to the first set of test pulses, determining a signal quality parameter based on the minimum value, and accepting the selected evoked response sensing electrode pair in response to the signal quality parameter.

12. The system of claim 11 wherein determining the signal quality parameter includes determining a ratio of the minimum value of the maximum signal amplitudes corresponding to the first set of test pulses and a predetermined first threshold.

13. The system of claim 12, wherein the processor:
compares the signal quality parameter to a predetermined second threshold; and
adjusts the first threshold in response to the signal quality parameter being less than the second threshold.

14. The system of claim 11 wherein the processor determines a maximum value of the determined maximum signal amplitudes corresponding to the second set of test pulses.

15. The system of claim 14 wherein determining the signal quality parameter includes determining a ratio of the maximum value of the maximum signal amplitudes corresponding to the second set of test pulses and a predetermined first threshold.

16. The system of claim 15 wherein the processor:
compares the signal quality parameter to a predetermined second threshold; and
adjusts the first threshold in response to the signal quality parameter being greater than the second threshold.

17. The system of claim 14 wherein determining the signal quality parameter includes determining a ratio of the minimum value of the maximum signal amplitudes corresponding to the first set of test pulses and the maximum value of the maximum signal amplitudes corresponding to the second set of test pulses.

18. The system of claim 11 wherein determining the signal quality parameter further includes determining, from the received signal in association with the first set of pulses, one of:
a time corresponding to the maximum signal amplitude of the sensed signal,
a capture detection time, and
a number of signal peaks.

19. The system of claim 11 wherein the processor determines a signal quality parameter for an alternate sensing electrode pair selected by the switching circuitry, and identities an optimal sensing electrode pair in response to the determined signal quality parameter for the alternate sensing electrode pair and the signal quality parameter for the selected evoked response sensing electrode pair.

20. A computer readable medium for storing a set of instructions which when implemented in an implantable medical device system cause the system to:
select an evoked response sensing electrode pair;
deliver a sequence of test pulses including a first set of test pulses having a first pulse energy exceeding a capture threshold and a second set of test pulses having a second pulse energy less than the capture threshold;
set a capture detection time window following each test pulse during which a signal is sensed using the selected evoked response sensing electrode pair;
determine a maximum signal amplitude of the sensed signal occurring during the capture detection window following each test pulse;
determine a minimum value of the determined maximum signal amplitudes corresponding to the first set of test pulses;
determine a signal quality parameter based on the minimum value of the determined maximum signal amplitudes corresponding to the first set of test pulses; and
accept the selected evoked response sensing electrode pair in response to the signal quality parameter.

21. The computer readable medium of claim 20 further comprising instructions which cause the system to:
select at least one alternate sensing electrode pair,
determine a signal quality parameter for the alternate sensing electrode pair,
and select an optimal sensing electrode pair based on the signal quality parameter for the alternate sensing electrode pair and the signal quality parameter for the selected evoked response sensing electrode pair.

22. The computer readable medium of claim 20 further comprising instructions which cause the system to:
  detect capture;
  and wherein determining the signal quality parameter includes determining, from the signal sensed during the capture detection time window corresponding to the first set of pulses, one of a time of maximum signal amplitude, a time of capture detection, and a number of signal peaks.

23. The computer readable medium of claim 20 further comprising instructions which cause the system to determine a maximum value of the maximum signal amplitudes corresponding to the second set of test pulses and wherein the instructions for determining the signal quality parameter include instructions for determining the signal quality parameter based the maximum value.

* * * * *